United States Patent [19]

Weimar

[11] Patent Number: 4,883,695
[45] Date of Patent: Nov. 28, 1989

[54] OPERATION TABLE COVER

[75] Inventor: Albert Weimar, Rosenheim-Pang, Fed. Rep. of Germany

[73] Assignee: SENGEWALD Klinikprodukte GmbH, Rohrdorf/Thansau, Fed. Rep. of Germany

[21] Appl. No.: 191,166

[22] Filed: May 2, 1988

[30] Foreign Application Priority Data

May 12, 1987 [DE] Fed. Rep. of Germany ....... 3715691

[51] Int. Cl.$^4$ .......................... B65D 30/00; B31B 1/64
[52] U.S. Cl. .................................... 428/35.2; 383/107; 428/36.1; 428/192; 428/124; 428/224; 493/189; 493/935
[58] Field of Search ................. 428/35, 192, 224, 124, 428/35.2, 36.1; 383/107, 119; 493/189, 935

[56] References Cited

U.S. PATENT DOCUMENTS

| | | | |
|---|---|---|---|
| 4,041,851 | 8/1977 | Jentsch | 383/107 |
| 4,674,129 | 6/1987 | Janhoven | 383/107 |
| 4,770,911 | 9/1988 | Sengewald | 428/35 |

Primary Examiner—Ellis P. Robinson
Assistant Examiner—James J. Seidleck
Attorney, Agent, or Firm—Michael J. Striker

[57] ABSTRACT

An operation table cover comprises a hose of a thermoplastic foil material, and having a bottom end which is closed and an opposite head end with which it is slippable over a supporting surface of an operation table, and two strips overlapping the head end of the hose at its two sides, the hose having a predetermined width, the overlapping strips having a width which in an unstretched condition of the overlapping strips is greater than the width of the hose.

4 Claims, 2 Drawing Sheets

OPERATION TABLE COVER

The invention relates to an operation table cover comprising a hose of a thermoplastic foil closed at its bottom end and provided at its opposite open head end with an overlapping strip at each hose wall, the head end of the hose being slippable over a supporting surface of operation table, the hose top side being provided with a coating made of an adsorptive non-woven fabric, and the width of the overlapping strips at the head end being larger than the remaining part of the hose.

An operation table cover of the foregoing configuration is described in the U.S. patent application Ser. No. 865,543. In case of said known cover, the larger width of the folds is obtained in that, relative to the remaining part of the hose, the inner hose width in the fold region is stretched to become permanently expanded. The stretching of the head end requires a mechanical device arranged within the hose and operable with difficulty. Further, dependent upon the foil material forming the operation table cover, it is not easy to achieve an always uniform stretching because the yield strength of the foil material must be exceeded and is also dictated by the foil material and the respective temperature.

It is the object of the instant invention to provide an operation table cover comprising a larger width of the overlapping strips obtainable safely and by simple means, so that the folded portion of the operation table cover may be inserted into the upper fold. This problem is solved according to the invention in that the larger width of the overlapping strips at the head end is obtained by providing for the overlapping strips a foil material being dimensioned in unstretched condition more widely than the remaining part of the hose. Since a broader dimension of the strips is realised without stretching, the strips are now uniformly dimensioned of a sufficient larger width, so that the insertion of the folded portion of the operation table cover under one of said strips is simply realisable.

According to another embodiment, it is suggested that two side edges of the strips are connected by welding. In other words, the lateral edges of the strips which extend in parallel to but are spaced from the side edges of the hose, are first open and not directly interconnected. By this means, it is not only easier to turn them outwardly, but also to insert parts of the operation table cover into one of the folds. If necessary, said handling may be also mechanized by simple means.

Moreover, pursuant to a further development, it is proposed to provide the hose side edges with lateral welding seams outside the region of the strips. Thus, a width which is larger than the remaining part of the operation table cover may be simply imparted to the strips.

Further, the lateral welding seams of the hose may be inwardly offset relative to the lateral welding seams of the folds, and, in this connection, it is particularly preferable to ensure that the lateral welding seams of the hose merge with those of the folds by a round transition.

The basic proposal of the invention may be realised in that the bottom is formed by a fold of the two hose walls. In such a case, a special welding means for closing the bottom need not be provided.

According to another embodiment of the invention, it is suggested to form two strips which extend transversely to the hose and whose external edges are connected by welding seams to the hose opening edges, the strips being provided with the mentioned lateral welding seams, and the bottom end of the walls being joined by a bottom seal. By this means, the operation table cover is formed of a hose whose width is used unchanged, the strip dimension being sufficiently broad by separately added strips so that the insertion of folded hose portions under one of the strips is easily possible.

The invention will be now explained in detail with reference to the drawings in which

BRIEF DESCRIPTION OF DRAWINGS:

The operation table cover 10 comprises two hose walls 11 and 12 such as particularly clearly recognizable from the sectional view of FIG. 4. At the bottom end 13, the hose walls include a fold. The side edges of the hose walls 11 and 12 are connected by longitudinal lateral welding seams 14 and 15, of which seam 14 may be seen in FIG. 1, while seam 15, on the other side, is evident from FIG. 5. The open head end of the operation table cover is provided with two folded strips 16 and 17 which, as evident from the embodiments of FIG. 1 to 7, are integrated with the hose walls 11 and 12. FIG. 2 shows the operation table cover provided, in use, on its surface with a non-woven fabric layer 18. The cover is slipped over the operation table 19 provided with feet 20 and 21.

As obvious from FIG. 5, the width B of the head end of the operation table cover is considerably larger than the subsequent region. The initial hose has the original width B. Then the edges are cut away from the longitudinal edge areas, and the lateral welding seams 14 and 15 are made. FIG. 5 also shows that the bottom end of the initial hose is closed by a transverse bottom welding seam 22 and that the lateral welding seams 14, 15 merge via round transitions 14a, 15a with the lateral folding lines of the closed hose.

Figure 1:
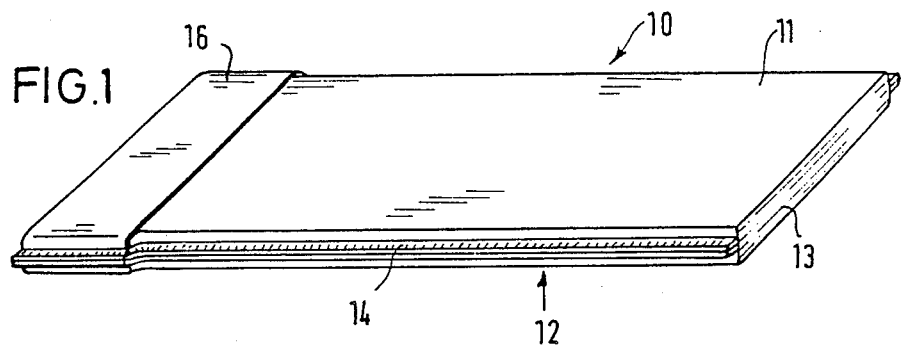
FIG. 1 shows a perspective view of an operation table cover.
Figure 2:
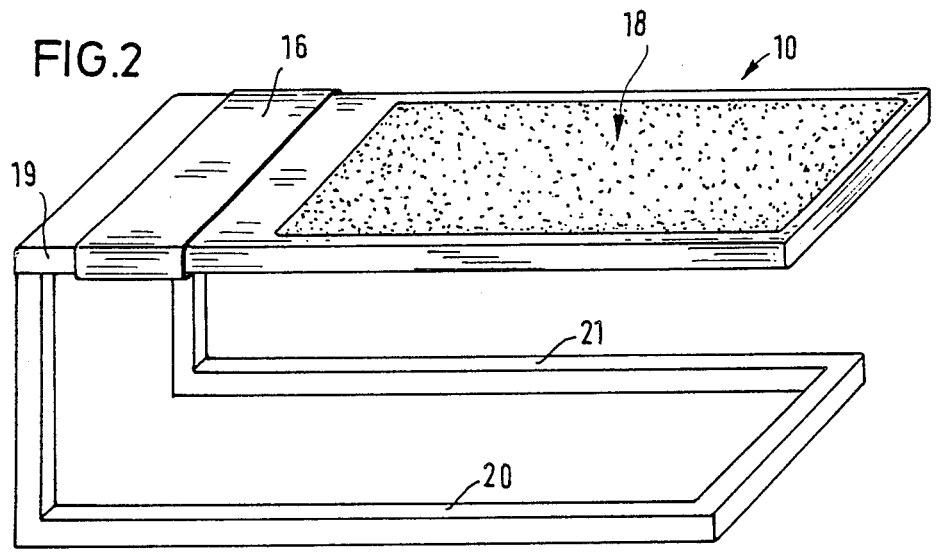
FIG. 2 shows the cover of FIG.1, slipped over an operation table.
Figure 3:
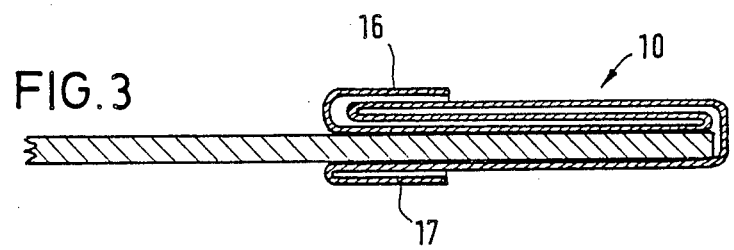
FIG. 3 is a vertical sectional view of the table plate with the cover partly slipped thereover.
Figure 4:
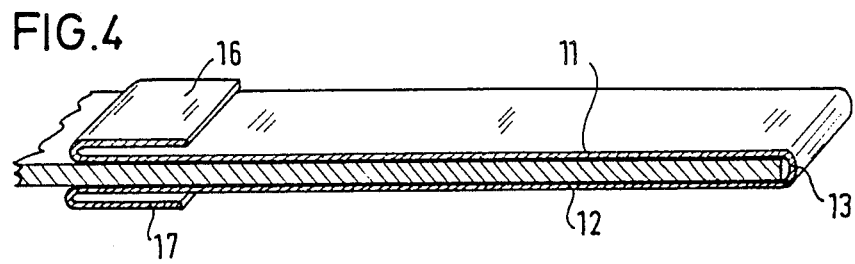
FIG. 4 is a vertical sectional view of the table plate with the cover completely slipped thereover.
Figure 5:
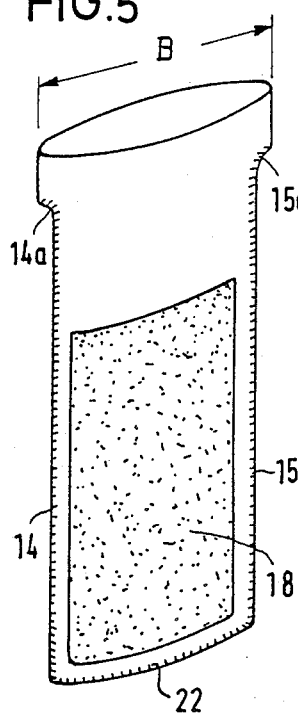
FIG. 5 is a perspective view of the operation table cover.
Figure 6:
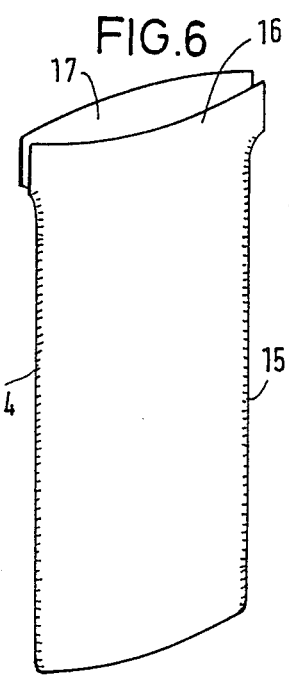
FIG. 6 is a perspective view of a modification of the operation table cover of FIG. 5.
Figure 7:
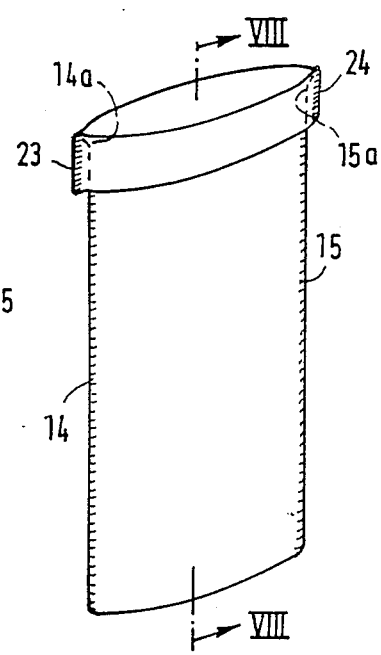
FIG. 7 shows the operation table cover of FIG. 6 with two strips in a final form.
Figure 8:
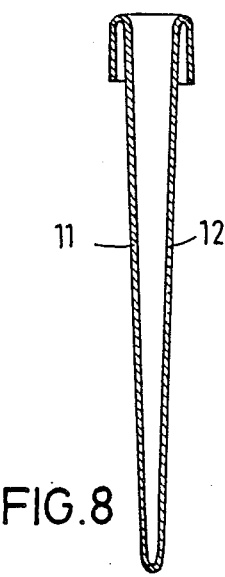
FIG. 8 is a sectional view of the operation table cover according to FIG. 7 corresponding to line VIII—VIII of the said Fig.

The modified operation table cover of FIG. 6 shows that, in accordance with the embodiment of FIG. 1, the bottom end is formed by a fold without a bottom welding seam 22. In the initial position of the strips 16 and 17 of FIG. 6, the side edges are not yet closed, contrary to the embodiment of FIG. 5. After the strips have been turned down, according to FIG. 7, they are connected with lateral welding seams 23 and 24 which considerably project to the outside laterally beyond the lateral welding seams 14 and 15. The round transitions 14a and 15a, such as in FIG. 5, are provided at the upper ends of welding seams 14 and 15 for merging with the lateral welding seams 23 and 24.

Figure 9:
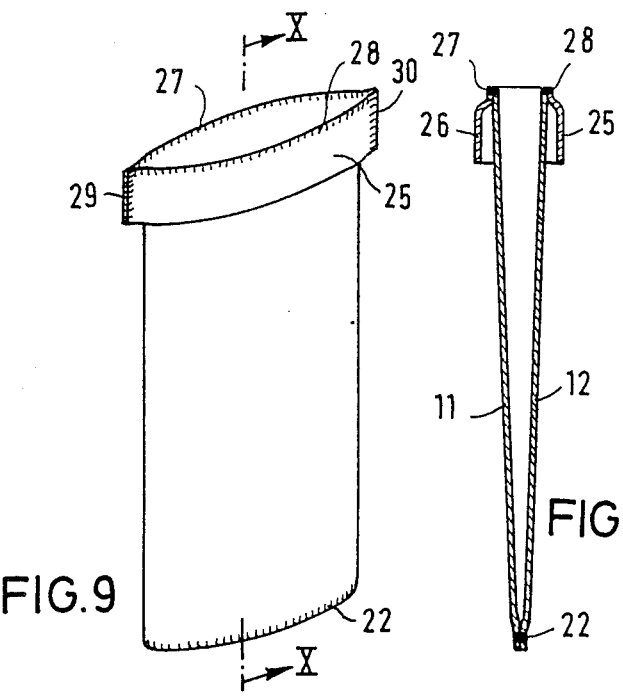
FIG. 9 shows another embodiment of the operation table cover with two strips.
Figure 10:
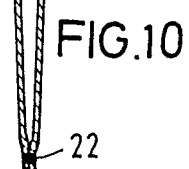
FIG. 10 is a sectional view of the operation table cover of FIG. 9 corresponding to line X—X of said Fig.

FIG. 9 shows a modified solution according to which a hose including walls 11 and 12 of a uniform width is used which, at its bottom end, is closed by a seam welding 22. The head end has no integrally formed strips, but there are strips 25 and 26 of a separate foil material. The upper edges of the strips 25 and 26 are connected by transverse weldings 27 and 28 to the associated hose walls 11 and 12. The lateral edges of the strips 25 and 26 are closed by lateral welding seams 29 and 30 extending lengthwise of the hose outside and in parallel with the lateral folds of the hose.

What is claimed is:

1. An operation table cover, comprising a hose of a thermoplastic foil material, said hose having a bottom end which is closed and an opposite head end with which it is slippable over a supporting surface of an operation table, said hose having two walls each having two lateral edges, said lateral edges of one of said walls being connected with said lateral edges of the other of said walls by first welding seams, said hose having an upper surface; a coating of an absorptive non-woven fabric provided on said upper surface of said hose; and two strips overlapping said head end of said hose at its two opposite sides, said hose having a predetermined width, said overlapping strips having a width which in an unstretched condition of said overlapping strips is greater than the width of said hose, said strips having two lateral edges, said two lateral edges of one of said strips being connected with said two lateral edges of the other of said strips by two second welding seams which are separate from said first welding seams and are located laterally outside of said first welding seams.

2. An operation table cover as defined in claim 1, wherein one of said walls of said hose merges into the other of said walls of said hose in the region of said bottom end, so that in the region of said bottom end said walls are integral and one piece with one another.

3. A method of manufacturing an operation table cover, comprising the steps of making a hose of a thermo-plastic foil material with a bottom end which is closed and with an opposite open head end with which the hose is slippage over a supporting surface of an operation table, wherein the hose has two walls each with two lateral edges; applying a coating of an absorptive non-woven fabric on an upper surface of said hose; forming two overlapping strips in the region of said open head end of the hose at both sides of the hose so that the overlapping strips in an unstretched condition have a width which is greater than the width of the hose and each strip has two lateral edges; connecting the lateral edges of the walls of the hose with two first welding seams; and connecting the lateral edges of the strips with two second welding seams which are separate from the first welding seams and located laterally outside the first welding seams.

4. A method as defined in claim 3, wherein said making step includes forming the hose so that in the region of the bottom end one of the walls merges into the other wall and said walls are integral and of one piece with one another.

* * * * *